United States Patent [19]

Hietaniemi et al.

[11] Patent Number: 4,579,970

[45] Date of Patent: Apr. 1, 1986

[54] 1-(4′-ALKYLAMIDO)-2′{1[N-(ALKYL-)IMINO]-ETHYL}-PHENOXY-3-ALKYLAMINO-2-PROPANOLS AND USE THEREOF

[75] Inventors: Lauri A. Hietaniemi, Kangastie; Heikki E. Nupponen, Ukinjärvi, both of Finland

[73] Assignee: Oy Star AB, Finland

[21] Appl. No.: 622,224

[22] Filed: Jun. 19, 1984

[30] Foreign Application Priority Data

Jun. 29, 1983 [FI] Finland .................. 8312377

[51] Int. Cl.$^4$ .................................. C07C 103/38
[52] U.S. Cl. ........................................ 564/223
[58] Field of Search .......................... 564/223

[56] References Cited

U.S. PATENT DOCUMENTS

| | | | |
|---|---|---|---|
| 3,284,490 | 11/1966 | Baltzly et al. | 564/223 X |
| 3,634,511 | 1/1972 | Howe et al. | 564/233 X |
| 3,726,919 | 4/1973 | Wooldridge et al. | 564/223 X |
| 3,875,149 | 4/1975 | Wooldridge et al. | 564/223 X |

FOREIGN PATENT DOCUMENTS 1231783 5/1971 United Kingdom ............. 564/223

*Primary Examiner*—Paul F. Shaver
*Attorney, Agent, or Firm*—McGlew and Tuttle

[57] ABSTRACT

The present invention concerns new (R)-, (S)- and (R,S)-1-(4′-alkylamido)-2′-{1-[N-(alkyl)imino]ethyl} phenoxy-3-alklyamino-2-propanols having the general formula

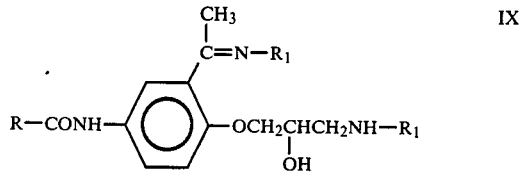

wherein R means a straight or branched $C_1$–$C_4$-alkyl group, especially the n-propyl group, and $R_1$ means hydrogen or a straight or branched $C_1$–$C_4$-alkyl group, especially the isopropyl group, which compounds are useful intermediates when preparing the pharmacologically active (R)-, (S)- and (R,S)-1-(4′-alkylamido-2′-acetyl)phenoxy-3-alkylamino-2-propanols of the formula

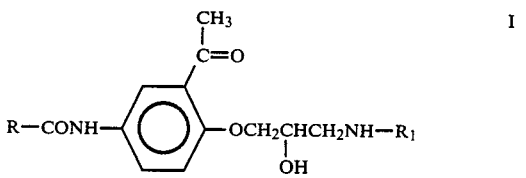

wherein R and $R_1$ have the meaning given above.

16 Claims, No Drawings

1-(4'-ALKYLAMIDO)-2'-{1-[N-(ALKYL)IMINO]-ETHYL}-PHENOXY-3-ALKYLAMINO-2-PROPANOLS AND USE THEREOF

The present invention concerns new imino-intermediate compounds, particularly (R)-, (S)- and (R,S)-1-(4'-alkylamido)-2'-{1-[N-(alkyl)imino]ethyl}phenoxy-3-alkylamino-2-propanols having the general formula

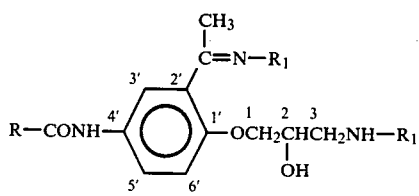

wherein R means a straight or branched $C_1$-$C_4$-alkyl group, preferably the n-propyl group, and $R_1$ means hydrogen or a straight or branched $C_1$-$C_4$-alkyl group, preferably the isopropyl group.

The new compounds of the formula IX are useful for the preparation, either as enantiomers or as a racemic mixture, of 1-(4'-alkylamido-2'-acetyl)phenoxy-3-alkylamino-2-propanols and their acid addition salts having the general formula I

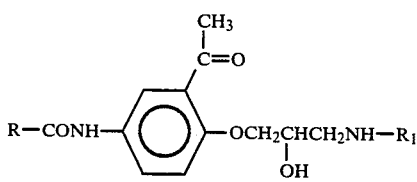

wherein R and $R_1$ have the meanings given above.

In the above formulas R and $R_1$ may be the same or different. The center of asymmetry of the compounds of the formula I and IX is situated at the carbon atom in 2-position.

Some of the compounds of the formula I have valuable pharmacological properties. One such a compound is 1-(4'-n-butyramido-2'-acetyl)phenoxy-3-isopropylamino-2-propanol (formula I, R=n-propyl, $R_1$=isopropyl) which is a valuable cardioselective β-blocking agent known as acebutolol.

The preparation of the compounds of the formula I is described in the GB-patent specification 1 247 384, according to which an epoxide of the formula II

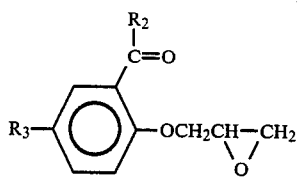

wherein $R_2$ means an alkyl group and $R_3$ means an alkanoyl amino group, is reacted with an amine having the above formula III, wherein $R_4$ means e.g. an alkyl group, in an inert solvent, such as ethanol or dimethylformamide at a temperature of 0° to 100° C., whereby compounds of the formula I are obtained.

When as starting materials on epoxide of the formula II, wherein $R_2$ is the methyl group and $R_3$ is the n-butyramido group, as well as an amine of the formula III, wherein $R_4$ is the isopropyl group, are used a compound of the formula I, wherein R is the n-propyl group and $R_1$ is the isopropyl group, i.e. acebutolol, is obtained with a yield of only 15% (cf the patent specification, Example 4).

In the U.S. Pat. No. 3,875,149 is described the preparation of oximes corresponding to the formula I and having the formula IV

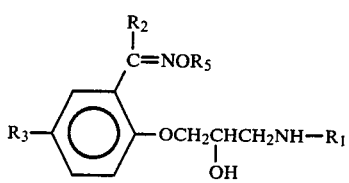

wherein $R_1$–$R_3$ mean e.g. the same as above and $R_5$ means e.g. hydrogen or an alkyl group, whereby as the starting material epoxides of the formula II are used, wherein $R_2$ and $R_3$ have the same meaning as above. The reaction is carried out in two steps by first reacting the epoxide of the formula II with a hydroxylamine of the formula V $$R_5ONH_2 \qquad V$$

wherein $R_5$ has the meaning given above, and the oximeepoxide thus obtained of the formula VI

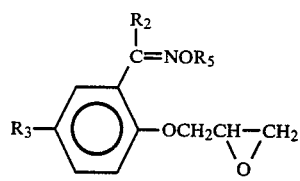

wherein $R_2$, $R_3$ and $R_5$ have the meaning given above, is converted to the oxime of the formula IV by reacting the same with an amine of the formula III in an inert solvent. According to the said patent specifications the compounds of the formulas I and IV have been prepared only as racemic mixtures.

The present invention allows for the preparation of the compounds of the formula I by reacting a compound having the general formula VII

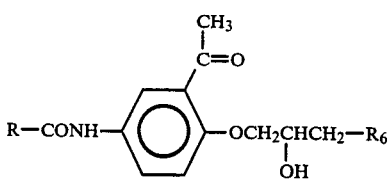

wherein R has the meaning given above and $R_6$ means a hydroxy group or a group which is easily replacable by an amine, such as halogen (chlorine or bromine) or an activated hydroxy group, such as a mesyloxy, benzenesulphonyloxy or p-toluenesulphonyloxy group and which may be in optically active form, i.e. of (R)- or (S)-configuration, or a racemic mixture, i.e. of (R,S)-configuration, with an amine having the formula VIII $$R_1-NH_2 \qquad VIII$$

wherein R₁ has the meaning given above, whereby the new compounds of the invention having the formula IX given above are obtained as intermediates. Advantageous with regard to yield has proven to be the activation of the compound of the formula VII, wherein R₆ is hydroxy, to form the corresponding tosylate (formula VII, R₆=p—CH₃—C₆H₄SO₂—O—) prior to reacting the latter compound with the amine of the formula VIII. This tosylation reaction is preferably performed in a cold pyridine solution at a temperature of 0° to 15° C.

It has now surprisingly turned out that when a compound of the formula VII, wherein R has the meaning given above and R₆ preferably means halogen, a mesyloxy, benzenesulphonyloxy or p-toluenesulphonyloxy group, is reacted with an amine of the formula VIII at a temperature of 0° to 100° C. without an auxiliary solvent or in the presence of an inert auxiliary solvent, such as water, chloroform, dimethylformamide, or dimethylsulphoxide, in addition to the expected replacement of the said group R₆ with the amine, also the surprising reaction takes place according to which the carbonyl group in the 2'-acetyl group in the compound of the formula VII reacts with the amine present, thus forming the above defined imine i.e. the Schiff base of the formula IX, wherein R and R₁ have the meanings given.

The imines of the formula IX, the racemic mixtures as well as the optical enantiomers of which are new compounds, may easily be hydrolyzed to the compounds of the formula I by dissolving the same into an inert solvent, such as a lower alcohol, e.g. methanol, ethanol or isopropanol, or a lower ketone, such as acetone or methyl ethyl ketone or dimethylformamide, or into a solvent mixture, such as a mixture of alcohol and water, and adjusting the pH of the solution to about 6–7 with an acid, such as a strong mineral acid, e.g. hydrochloric acid or sulphuric acid, whereby the acid addition salt of the amine of the formula I is obtained. The corresponding base may be liberated from the salt in a known manner by dissolving the salt into an inert solvent such as water, and adjusting the pH of the solution to about 9 with a suitable base, such as an alkali carbonate or hydroxide, whereafter the liberated base is recovered by filtering or by extracting into an inert organic solvent, such as chloroform or ether, and evaporating the solvent.

The diols of the formula VII, wherein R₆ is hydroxy, used as starting material for the preparation of the new intermediate compounds of the formula IX, may be prepared by methods known from literature. One such method comprises reacting a 5-alkylamido-2-hydroxy-acetophenon of the formula X

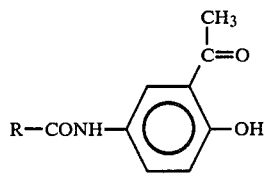

wherein R has the meaning given above and which in turn may be prepared by a method described in an article by Julia et al in Bull. Soc. Chim. Fr. 1952, or more advantageously an alkali metal salt thereof with a 3-halo-1,2-propane diol of the formula XI

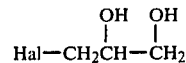

which is of (R,S)-, (R)- or (S)-configuration, wherein Hal means chlorine or bromine, under alkaline conditions, at a temperature of 20° to 100° C. and in the presence of an inert solvent, such as methanol, ethanol, isopropanol, dimethylformamide, methylene chloride etc., and isolating the product by evaporating the neutralized reaction mixture. The (R,S)-3-halo-1,2-propane diols of the formula XI are commercial substances, whereas the (R)- and (S)-isomers may be prepared e.g. as described in the article of Jones in Chem. Ind. 15:533, (1978).

According to a further method of preparing the diols of the formula VII as intermediates a glycerol acetonide of the formula XII is used

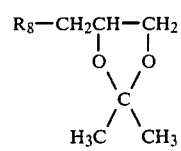

wherein R₈ means a hydroxy group and which compound may be of (R)-, (S)- or (R,S)-configuration and which may be prepared from commercially available serine of the corresponding configuration according to Lok et al., Chemistry and Physics of Lipids 16:115 (1979). From the glycerol acetonide of the formula XII the diol of the formula VII is obtained by replacing first the group R₈ with an easily replacable group, such as chlorine, bromine, mesyloxy, benzenesulphonyloxy or p-toluenesulphonyloxy group, and reacting the thus formed compound with a phenol of the formula X, or more advantageously, with its alkali metal salt, in an inert solvent, such as dimethylformamide, ethanol or isopropanol at a temperature of 20° to 140° C.

The acetonide thus obtained having the formula XIII

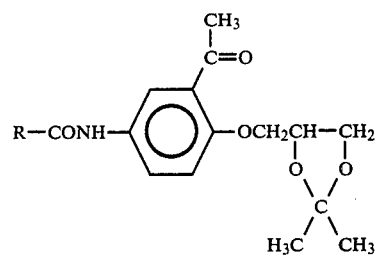

wherein R has the meaning given above, may easily be hydrolyzed to the diol of the formula VII of (R)-, (S)- or (R,S)-configuration, wherein R₆ means a hydroxy group, by treatment in an acid solution at a temperature of 20° to 100° C. Acids suitable for this purpose are for example hydrochloric acid, sulphuric acid, phosphoric acid, nitric acid, formic acid and acetic acid, as well as their aqueous solutions. As an auxiliary solvent also an inert organic solvent may be used, if desired.

According to the process described the compounds of the formula I, such as acebutolol, may be advantageously prepared as a racemic mixture as well as enantioselectively as (R)- or (S)-enantiomers via the new imines of the formula IX. According to the British patent specification 1 247 384 only racemates can be prepared.

All the necessary starting materials are commercially available and reasonable priced. All intermediate and end products are easily recovered from their reaction mixtures and obtainable already as raw products in a fairly pure form and may, if needed, be easily purified further. When using optical enantiomers, no racemization has been observed when carrying out the reaction steps of the invention.

The following examples illustrate the invention. The structure of the relevant compounds has been confirmed with H$^1$-NMR-, IR- and mass spectra. The melting points have been corrected.

EXAMPLE 1

(S)-1-(4'-butyramido-2'-acetyl)phenoxy-3-isopropylamino-2-propanol (Formula 1; R=n-propyl, R$_1$=isopropyl)
(=(S)-acebutolol)

a. Sodium salt of 5-butyramido-2-hydroxyacetophenon 66.4 g (0.30 moles) of 5-butyramido-2-hydroxyacetophenon is dissolved in 460 ml of tetrahydrofurane and to the solution is gradually added at room temperature 24.3 g of a 47% aqueous solution of sodium hydroxide. The precipitate formed is separate by filtration and washed with tetrahydrofurane and dried. Yield 70.8 g (97% of theor.) of yellow, crystalline sodium salt of 5-butyramido-2-hydroxy-acetophenon.

b. 2,3-acetonide of (S)-1-(4'-butyramido-2'-acetyl)phenoxy-2,3-propanediol (Formula XIII; R=n-propyl)

49.9 g (0,205 moles) of the sodium salt of 5-butyramido-2-hydroxyacetophenon and 54.4 g (0.19 moles) of (S)-3-p-toluenesulphonyloxy-1,2-propanediol-1,2-acetonide (formula XII; R$_8$=p-toluenesulphonyloxy) are dissolved while stirring into 250 ml of dimethylformamide and mixed for 7 h at 100° C. About half of the dimethylformamide is evaporated in vacuum and to the residue 600 ml of water is added and mixed for 1 h while cooling (<10° C.). The precipitate is filtered, washed with water and dried. Yield is 51.0 g (80% of theor.) of (S)-1-(4'-butyramido-2'-acetyl)-phenoxy-2,3-propanediol-2,3-acetonide.

NMR (CDCl$_3$); δ1.0 (t, 3H, J=7 Hz), δ1.45 (s, 3H), δ1.50 (s, 3H), δ2.60 (s, 3H), δ6.7–8.2 (m, 3H)

c. (S)-1-(4'-butyramido-2'-acetyl)phenoxy-2,3-propanediol (Formula VII; R=n-propyl, R$_6$=hydroxy)

50.3 g (0.15 moles) of (S)-1-(4'-butyramido-2'-acetyl)-phenoxy-2,3-propanediol-2,3-acetonide is mixed in 500 ml of 80% acetic acid for 2.5 h at about 70° C., whereafter the mixture is concentrated to about 80 ml and 400 ml of ether is added and mixed for 10 min. The precipitate is separated by filtration and washed with ether and dried. Yield 32.8 g (74% of theor.) of (S)-1-(4'-butyramido-2'-acetyl)phenoxy-2,3-propanediol.

NMR (CD$_3$)$_2$SO); δ1.0 (t, 3H, J=7 Hz), δ2.65 (s, 3H), δ7.0–8.0 (m, 3H)

d. (R)-1-(4'-butyramido-2'-acetyl)phenoxy-3-p-toluenesulphonyloxy-2-propanol (Formula VII; R=n-propyl, R$_6$=p-toluenesulphonyloxy)

26.3 g (0.089 moles) of recrystallized (S)-1-(4'-butyramido-2'-acetyl)phenoxy-2,3-propanediol is dissolved in 275 ml of pyridine and to the solution is gradually dropped within about 3 hours 17.0 g (0.089 moles) of p-toluenesulphonylchloride in 190 ml of methylene chloride while mixing and cooling at ≦−10° C. After the addition the mixture is allowed to warm to room temperature within about 16 h while stirring. From the reaction mixture the pyridine is distilled off under vacuum and the residue is dissolved in 500 ml of methylene chloride. The solution is washed with 100 ml of 1N hydrochloric acid and 40 ml of a 1M sodium carbonate solution, dried with magnesium sulphate and filtered. The filtrate is evaporated to dryness under vacuum, whereby 29.2 g (73% of theor.) of (R)-1-(4'-butyramido-2'-acetyl)phenoxy-3-p-toluenesulphony-oxy-2-propanol is obtained. M.p. 108°–110° C. (toluene-isopropanol). [α]$_D^{25}$= +19.9° C. (methanol).

NMR (CDCl$_3$); δ1.0 (t, 3H, J=7 Hz), δ2.4 (s, 3H), δ2.45 (s, 3H), δ6.6–8.0 (m, 7H)

IR (KBr); 3400, 3320, 1680, 1645, 1550, 1500, 1170 e. (S)-1-(4'-butyramido-2'-{1-[N-(isopropyl)imino]ethyl}phenoxy-3-isopropylamino-2-propanol (Formula IX; R=n-propyl, R$_1$=R$_7$=isopropyl)

25.2 g (0.056 moles) of (R)-1-(4'-butyramido-2'-acetyl)phenoxy-3-p-toluenesulphonyloxy-2-propanol and 125 ml of isopropylamine is mixed for 16 h at room temperature and the excess isopropylamine is evaporated under vacuum. The residue is dissolved in 300 ml of methylene chloride and the solution is washed with 2×100 ml of water, dried on magnesium sulphate and filtered. The filtrate is evaporated to dryness under vacuum, whereby 19.0 g (90% of teor.) of (S)-1-(4'-butyramido)-2'-{1-[N-(isopropyl)imino]ethyl}phenoxy-3-isopropylamino-2-propanol is obtained.

NMR (CDCl$_3$); δ0.7–1.3 (m, 9H), δ2.2 (s, 3H), δ6.5–8.5 (m, 3H).

IR (KBr); 1680, 1650, 1610 (C=N), 1550, 1500, 1410, 1235, 1210

MS; (EI) M+1=378.

f. (S)-1-(4'-butyramido-2'-acetyl)phenoxy-3-isopropylamino-2-propanol-hydrochloride (Formula I; R=n-propyl, R$_1$=isopropyl)
(=(S)-acebutolol hydrochloride)

11.3 g (0.03 moles) of (S)-1-(4'-butyramido)-2'-{1-[N-isopropyl)imino]ethyl}phenoxy-3-isopropylamino-2-propanol-raw product is dissolved in 120 ml of methanol. To the solution is added 30 ml of water and the pH of the solution is adjusted to 6.5–6.8 with concentrated hydrochloric acid. The solution is evaporated to dryness under vacuum and the residue is crystallized from a mixture of acetone and ethanol (1:1 vol./vol.), whereby 10.3 g of (92% of theor). of colourless pure (S)-1-(4'-butyramido-2'-acetyl)phenoxy-3-isopropylamino-2-propanol hydrochloride is obtained. M.p. 133°–135° C. [α]$_D$=−12.9° C. (methanol). The optical purity measured with liquid chromatography (cf Silber & al., J. Pharm. Exp. Ther. 215(3):643 (1980) is over 98%.

NMR (D$_2$O); $\delta$1.0 (t, 3H, J=7 Hz), $\delta$1.50 (d, 6H, J=7 Hz), $\delta$1.7 (m, 2H, J=7 Hz), $\delta$2.3 (q, 2H, J=7 Hz), $\delta$2.65 (s, 3H), $\delta$6.8–7.8 (m, 3H).

IR (KBr); 3300, 1680, 1650, 1530, 1500, 1400, 1300, 1270, 1240, 1210, 1150, 1100, 1050, 1025, 810.

The (S)-acebutolol base may be liberated from the hydrochloride or other acid addition salt by dissolving the same in water and adjusting the pH of the solution to about 9 using a 10% sodium carbonate solution, whereafter the base is extracted into a suitable organic solvent, such as methylene chloride. The extract is washed with water, dried on magnesium sulphate and filtered and the the filtrate is evaported to dryness under vacuum. The residue is recrystallized from toluene, whereby the pure (S)-acebutolol base is obtained.

IR (KBr): 3340, 1690, 1650, 1540, 1495, 1295, 1230, 1215.

EXAMPLE 2

(R)-1-(4'-butyramido-2'-acetyl)phenoxy-3-isopropylamino-2-propanol hydrochloride (Formula 1; R=n-propyl, R$_1$=isopropyl)
(=(R)-acebutolol hydrochloride)

The (R)-entantiomer of acebutolol is prepared according to Example 1 using as the starting material in place of (S)-3-p-toluenesulphonyloxy-1,2-propanediol-1,2-acetonide the corresponding acetonide of (R)-configuration, whereby (R)-acebutolol-hydrochloride is obtained, which NMR- and IR-spectra are identical to those of the corresponding (S)-compound (cf Example 1, para f) and $[\alpha]_D = +12.6°$ C. (methanol). The (R)-acebutolol-hydrochloride may be converted to the corresponding base according to paragraph f in Example 1.

EXAMPLE 3

(R,S)-1-(4'-butyramido-2'-acetyl)phenoxy-3-isopropylamino-2-propanol (Formula 1; R=n-propyl, R$_1$=isopropyl)
(=(R,S)-acebutolol)

a.

(R,S)-1-(4'-butyramido-2'-acetyl)phenoxy-2,3-propanediol (Formula VII; R=n-propyl, R$_6$=hydroxyl)

A solution containing 15.1 g (0.062 moles) of the sodium salt of 5-butyramido-2-hydroxyacetophenon prepared according to paragraph a in Example 1, 13.7 g (0.124 moles) of (R,S)-3-chloro-1,2-propanediol (Formula XI; hal=chlorine) and 6.0 g of 85% potassium hydroxide in 75 ml of methanol, is refluxed for 8 h, cooled and neutralized with concentrated hydrochloric acid. The methanol is evaporated under vacuum and to the residue is added 200 ml of ethyl acetate and the mixture refluxed for 15 min. The mixture is filtrated while hot and the filtrate is allowed to cool to room temperature and 40 ml of n-hexane is slowly added, whereby the product gradually precipitates out. The precipitate is separated by filtering and dried. Yield 11.0 g (60% of theor.) of (R,S)-1-(4'-butyramido-2'-acetyl)-phenoxy-2,3-propanediol. M.p. 137°–139° C. (toluene-isopropanol). The NMR-spectrum of the product is identical to that of the corresponding (S)-compound (cf Example 1, paragraph c).

b.

(R,S)-1-(4'-butyramido-2'-acetyl)phenoxy-3-p-toleuensulphonyloxy-2-propanol (Formula VII; R=n-propyl, R$_6$=p-toluenesulphonyloxy)

(R,S)-1-(4'-butyramido-2'-acetyl)phenoxy-2,3-propanediol prepared according to the preceeding paragraph is treated according to Example 1d, whereby (R,S)-1-(4'-butyramido-2'-acetyl)phenoxy-3-p-toluenesulphonyloxy-2-propanol is obtained. M.p. 135°–137° C. (toluene-isopropanol). The NMR- and IR-spectra of the product are identical to those of the corresponding (S)-compound (cf Example 1, paragraph d).

c.

(R,S)-1-(4'-butyramido)-2'-{1-[N-(isopropyl)imino]ethyl}phenoxy-3-isopropylamino-2-propanol (Formula IX; R=n-propyl, R$_1$=R$_7$=isopropyl)

By treating (R,S)-1-(4'-butyramido-2'-acetyl)-phenoxy-3-p-toluenesulphonyloxy-2-propanol obtained in paragraph b in a manner according to Example 1, paragraph e, (R,S)-1-(4'-butyramido)-2'-{1-[N-(isopropyl)imino]ethyl}phenoxy-3-isopropylamino-2-propanol is obtained. M.p. 129°–131° C. (n-hexaneether). The NMR-, IR- and mass spectra of the compound are identical to those of the corresponding (S)-compound. (cf Example 1, paragraph e).

d.

(R,S)-1-(4'-butyramido-2'-acetyl)phenoxy-3-isopropylamino-2-propanol hydrochloride (Formula 1R=n-propyl, R$_1$=isopropyl)
(=(R,S)-acebutolol hydrochloride)

By treating (R,S)-1-(4'-butyramido-2'-{1-[N-(isopropyl)imino]ethyl}phenoxy-3-isopropylamino-2-propanol obtained in paragraph c in a manner according to Example 1f (R,S)-1-(4'-butyramido-2'-acetyl)-phenoxy-3-isopropylamino-2-propanol hydrochloride is obtained with a yield of about 90% M.p. 140°–142° C. (acetone-ethanol). The NMR- and IR-spectra of the compound are identical to those of the corresponding (S)-compound (cf Example 1, paragraph f).

(R,S)-acebutolol-base may be liberated from the hydrochloride by adjusting the pH of its aqueous solution to about 9 with a 10% sodium carbonate solution and extracting the base into an organic solvent, such as methylene chloride. The methylene chloride extract is washed with water, dried on magnesium sulphate, filtered and the filtrate is evaporated to dryness in vacuum. The residue is crystallized from toluene, whereby pure (R,S)-acebutolol-base is obtained with a yield of 95%,. M.p. 124°–125° C. The IR-spectrum of the product is identical to that of the corresponding (S)-compound (cf Example 1, paragraph f).

We claim:

1. (R)-, (S)- and (R,S)-1-(4'-alkylamido)-2'-{1-[N-(alkyl)imino]ethyl}phenoxy-3-alkylamino-2-propanols, characterized in that their general formula is

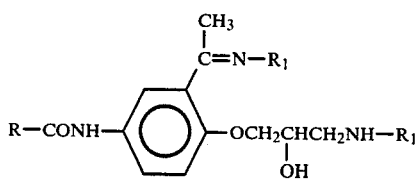

wherein R means a straight or branched $C_1$-$C_4$-alkyl group, and $R_1$ means hydrogen or a straight or branched $C_1$-$C_4$-alkyl group.

2. Compound according to claim 1, characterized in that in the formula IX R is the n-propyl group and $R_1$ is the isopropyl group.

3. Compound of claim 1 wherein each $R_1$ in the formula IX is the same straight or branched $C_1$-$C_4$-alkyl group.

4. Process for preparing (R)- (S)- and (R,S)-1-(4'-alkylamido)-2'-{1-[N-(alkyl)imino]ethyl}phenoxy-3-alkylamino-2-propanols having the general formula

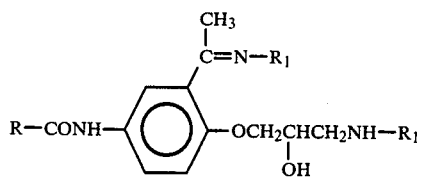

wherein R is a straight or branched $C_1$-$C_4$-alkyl group, and $R_1$ is hydrogen or a straight or branched $C_1$-$C_4$-alkyl group, which comprises reacting an amine of the formula $R_1$—$NH_2$ VIII in which $R_1$ has the same meaning as defined above, with an amine reactable compound having the general formula

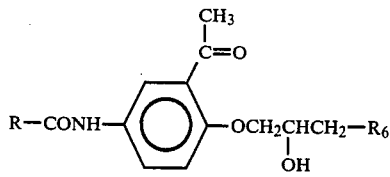

in which $R_6$ is an amine reactable group capable of forming a product with a hydrogen substituent of the amine of formula VIII whereby to form such compound of formula IX.

5. Process of claim 4, wherein the reaction is carried out in the absence of any auxiliary solvent.

6. Process of claim 4, wherein the reaction is carried out at a temperature of 0° to 100° C.

7. Process of claim 4, wherein the reaction is carried out at room temperature.

8. Process of claim 4, wherein the reaction is carried out in the presence of an excess of the amine of formula VIII and in the absence of any auxiliary solvent, and at a temperature of 0° to 100° C.

9. Process of claim 8, wherein the reaction is carried out at room temperature.

10. Process of claim 6, wherein $R_1$ is the isopropyl group.

11. Process of claim 4, wherein the compound of formula IX which is formed is converted to the corresponding pharmacologically active (R)-, (S)- and (R,S)-1-(4'-alkylamido-2'-acetyl) phenoxy-3-alkylamino-2-propanol having the formula

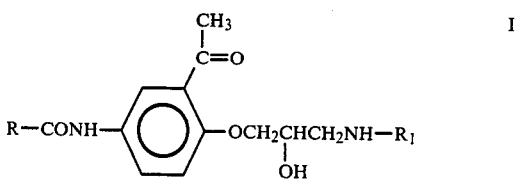

in which R and $R_1$ have the same meaning as defined above, or to the acid addition salts thereof, by correspondingly hydrolyzing such compound of formula IX.

12. Process of claim 11 wherein the hydrolyzing is carried out with an acid at a pH of about 6-7 to form the corresponding acid addition salt.

13. Process of claim 12, wherein the corresponding base is formed by adjusting a solution of such acid addition salt to a pH of about 9.

14. Process for preparing pharmacologically active (R)-, (S)- and (R,S)-1-(4'-alkylamido-2'-acetyl) phenoxy-3-alkylamino-2-propanols having the formula

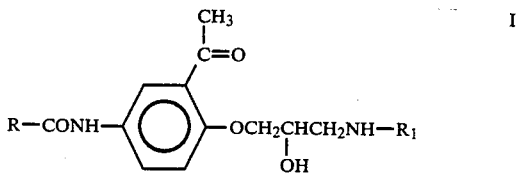

in which R is a straight or branched $C_1$-$C_4$-alkyl group and $R_1$ is hydrogen or a straight or branched $C_1$-$C_4$-alkyl group, or to the acid addition salts thereof, from compounds of formula IX of claim 1, which comprises correspondingly hydrolyzing such compound of formula IX.

15. Process of claim 14, wherein the hydrolyzing is carried out with an acid at a pH of about 6-7 to form the corresponding acid addition salt.

16. Process of claim 15, wherein the corresponding base is formed by adjusting a solution of such acid addition salt to a pH of about 9.

* * * * *